(12) United States Patent
Kim et al.

(10) Patent No.: US 6,369,037 B1
(45) Date of Patent: Apr. 9, 2002

(54) CONTROLLED RELEASE OF DOXORUBICIN

(75) Inventors: Sin-Hee Kim, Seoul (KR); Chih-Chang Chu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/677,859

(22) Filed: Oct. 3, 2000

Related U.S. Application Data

(60) Provisional application No. 60/160,211, filed on Oct. 19, 1999.

(51) Int. Cl.$^7$ .............................................. A61K 31/70
(52) U.S. Cl. ........................ 514/34; 424/486; 424/488
(58) Field of Search ............................ 514/34; 424/486, 424/488

(56) References Cited

U.S. PATENT DOCUMENTS

| | | | |
|---|---|---|---|
| 4,925,677 A | 5/1990 | Feijen | 424/484 |
| 5,334,640 A | 8/1994 | Desai et al. | 524/56 |
| 5,514,379 A | 5/1996 | Weissleder et al. | 424/426 |
| 5,700,848 A | 12/1997 | Soon-Shiong et al. | 522/7 |
| 5,736,161 A | 4/1998 | de los Santos Garces et al. | 424/493 |
| 5,846,530 A | 12/1998 | Soon-Shiong et al. | 424/93.7 |

OTHER PUBLICATIONS

Kim, S., et al., J. Biomed. Mater. Res. 49(4), 517–527 (3/2000).
Kim, S., et al., J. Biomaterials Applications 15(1), 23–46 (7/2000).
Matherne, C. M., et al., Am. J. Vet. Res. 55, No. 6, 847–853 (6/94).
Tonetti, M., et al., Am. J. Vet. Res. 52, No. 10, 1630–1635 (10/91).
Arap, W., et al., Science 279, 377–380 (1/98).
Gupta, P. K., et al., Life Sciences 46, 471–479 (1990).
Park, K., et al., Biodegradable Hydrogels for Drug Delivery, Technomic Publishing Co., Inc., Lancaster, Pa, 85–87 (1993).
van Dijk–Wolthuis, W. N. E., Macromolecules 30, 4639–4645 (1997).
Graham, N. B., et al., Biomaterials 5, 27–36 (1/84).
Hennink W. E., et al., J. Control. Release 39, 47–55 (1996).
Franssen, O., et al., J. Control. Release 44, 237–245 (1997).
Jones, C., et al., J. Pharm. Pharmacol. 41, 813–816 (6/89).

*Primary Examiner*—Elli Peselev

(57) ABSTRACT

A controlled release doxorubicin containing composition comprises doxorubicin physically entrapped in a dextran-methacrylate biodegradable hydrogel. The composition provides a rapid initial release of doxorubicin over a period of 5 to 7 hours followed by slow release. Increased degree of substitution in the dextran methacrylate decreases cumulative doxorubicin release. The composition provides higher cumulative release in acid pH (e.g., the stomach) than at physiological pH at lower degrees of substitution. The composition allows administration alternatives to the bolus intravenous and continuous intravenous methods of administration now used for doxorubicin. The composition can be prepared without the use of heat (which can result in heat destruction of doxorubicin) and is prepared without chemical cross-linker such as glutaraldehyde and the toxicity associated therewith.

12 Claims, 3 Drawing Sheets

CONTROLLED RELEASE OF DOXORUBICIN

CROSS-REFERENCE TO RELATED APPLICATION

This application claims the benefit of U.S. Provisional Application No. 60/160,211, filed Oct. 19, 1999, the whole of which is incorporated herein by reference.

TECHNICAL FIELD

This invention is directed at a composition for the controlled release of doxorubicin.

BACKGROUND OF THE INVENTION

Doxorubicin is a commonly used antineoplastic drug. Commonly responsive tumors include acute leukemia, Hodgkin's disease, other lymphoinas, breast and lung cancer. Doxorubicin has been reported to give a high response rate in the treatment of advanced breast cancer and to give favorable results for the treatment of gastric carcinoma (a tumor for which only four drugs are known to be active). However, doxorubicin has a narrow therapeutic index and causes cardiac toxicity at a cumulative dose of 450 to 550 mg/m$^2$. The usual dosage is 40–75 mg/m$^2$ rapidly intravenous or 30 mg/m$^2$ for three days by continuous IV. Alternative methods of administration have been sought which accommodate the narrow therapeutic index and cumulative dose toxicity. In particular, a controlled release form of doxorubicin has been sought, and glutaraldehyde treated erythrocytes and glutaraldehyde treated albumin have been suggested as carriers for this purpose. However, the glutaraldehyde can react with the doxorubicin causing the doxorubicin to become less active and is potentially toxic, and heat is used in glutaraldehyde treatment of albumin which can inactivate doxorubicin. Accordingly, a carrier for controlled release of doxorubicin has been sought where no chemical cross-linker is necessary and where beat is not involved in the preparation of the carrier.

SUMMARY OF THE INVENTION

The invention herein provides a composition for the controlled release of doxorubicin where the carrier is a dextran-methacrylate biodegradable hydrogel and where no chemical cross-linker or heat are necessary for the preparation of the carrier. The composition for the controlled release of doxorubicin comprises doxorubicin physically entrapped in a dextran-methacrylate biodegradable hydrogel. The composition is formed, for example, by photocrosslinking dextran methacrylate monoester in solution in a medium containing doxorubicin and drying, the dextran methacrylate monoester having an average degree of substitution of each α-D-glucopyranosyl of dextran by methacrylic acid ranging from 0.05 to 0.75 and a weight average molecular weight ranging from 40,000 to 80,000 on a dextran basis, e.g., 50,000 to 75,000 on a dextran basis, said medium being buffered to a pH ranging from 2 to 8, the weight ratio of doxorubicin to dextran methacrylate monoester ranging from 1:200 to 1:2000, e.g., from 1:500 to 1:1500.

In one subset of the invention, the dextran methacrylate monoester which is photocrosslinked has an average degree of substitution ranging from 0.05 to 0.15.

In another subset of the invention, the dextran methacrylate monoester which is photocrosslinked has an average degree of substitution ranging from 0.15 to 0.40.

In still another subset of the invention, the dextran methacrylate monoester which is photocrosslinked has an average degree of substitution ranging from 0.40 to 0.75.

The term "physically entrapped" is used herein to mean physically impregnated, i.e., the drug is within the hydrogel network but there has been no chemical reaction between the drug and the hydrogel network.

The term "hydrogel" is used herein to mean a polymeric material which exhibits the ability to swell in water and to retain a significant portion of water within its structure without dissolution.

The term "biodegradable hydrogel" is used herein mean hydrogel formed by cross-linking a polymer which is degraded by water and/or by enzymes found in the body.

The term "photocrosslinking" is used herein to mean causing vinyl bonds in the methacryloyl moieties to break and form cross-links by the application of radiant energy.

The term "degree of substitution" is used herein to mean the number of hydroxyl groups in a glucose unit of α-D-glucopyranosyl moiety of dextran that form ester group with methacrylic acid. Since each said glucose unit contains three hydroxyl groups, the maximum degree of substitution is 3.0. The average degree of substitution connotes the average degree of substitution based on all the glucose units in the molecules of dextran methacrylate monoester.

The term "on a dextran basis" is used herein to mean that the weight average molecular weight referred to is that of the dextran starting material for preparing the dextran methacrylate monoester which provides the dextran moiety of the dextran methacrylate monoester. The weight average molecular weights referred to herein are those determined on dextran by light scattering or gel permeation chromatography. In the working example herein, the dextran used to prepare the dextran methacrylate monoester was obtained from Sigma Chemicals, and had a weight average molecular weight of 70,000 determined by gel permeation chromatography; therefore, the dextran methacrylate monoester used in the working example herein had a weight average molecular weight of 70,000 on a dextran basis, determined by gel permeation chromatography.

DETAILED DESCRIPTION

Figure 1:
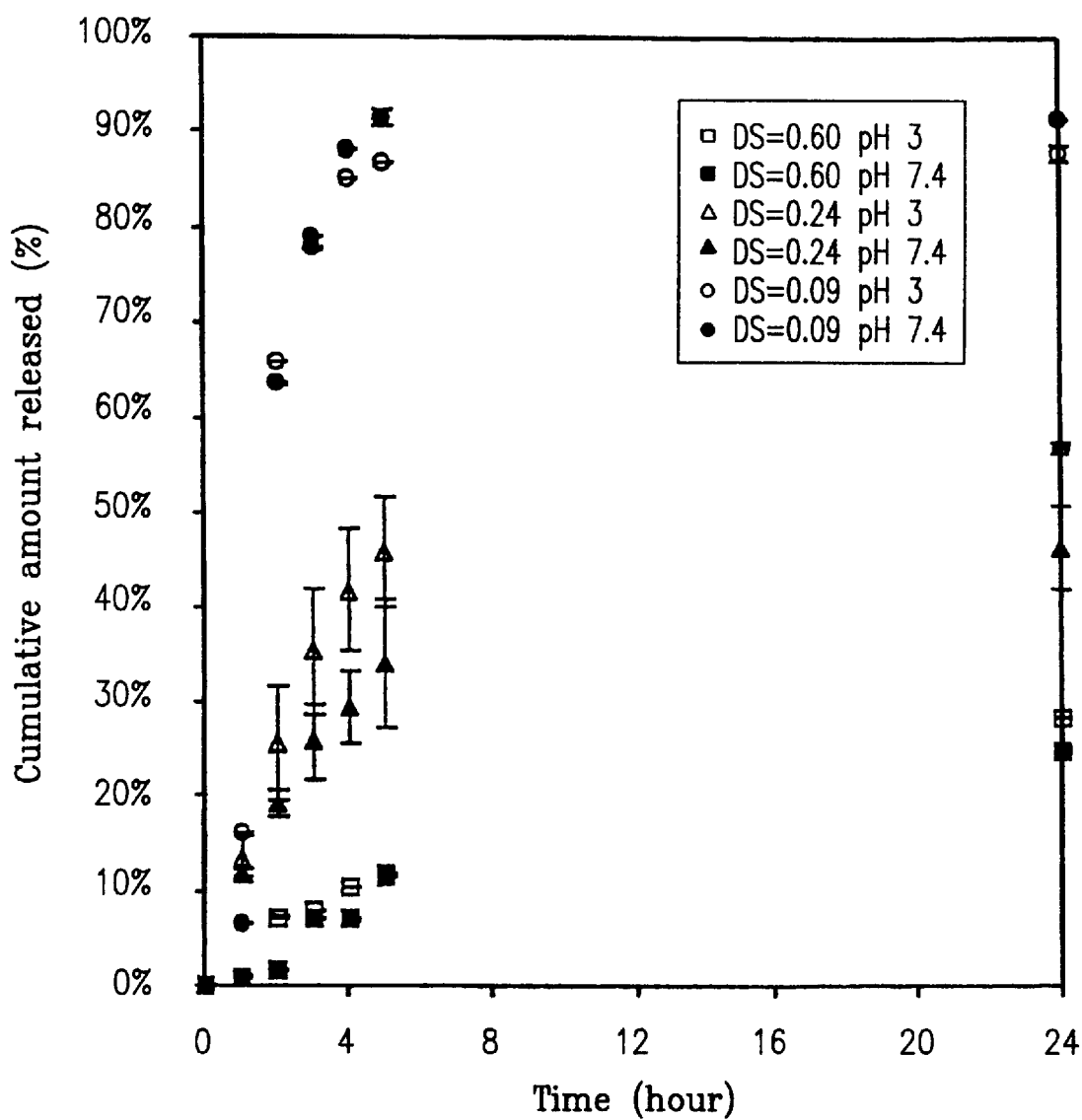
FIG. 1 is a graph depicting cumulative amount of doxorubicin released from dextran-methacrylate hydrogels having different degrees of substitution in different pH media at 1 hour, 2 hours, 3 hours, 4 hours, 5 hours and 24 hours, and shows results of Example I.

As indicated above, composition of the invention is formed, for example, by photocrosslinking dextran methacrylate monoester in solution in a medium containing doxorubicin and drying, the dextran methacrylate monoester having an average degree of substitution of each α-D-glucopyranosyl of dextran by methacrylic acid ranging from 0.05 to 0.75 and a weight average molecular weight ranging from 40,000 to 80,000 on a dextran basis, said medium being buffered to a pH ranging from 2 to 8, the weight ratio of the doxorubicin to dextran methacrylate monoester ranging from 1:200 to 1:2000, e.g., from 1:500 to 1:1500.

We turn now to the dextran methacrylate monoester starting material for preparing composition herein.

These compounds are exemplified by the formula

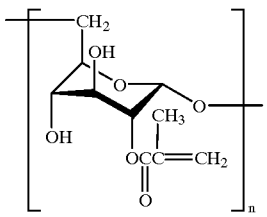

where n has a range providing the above-described molecular weight range, for a degree of substitution of 1.

The dextran methacrylate monoester is readily prepared by reaction of dextran with methacrylic anhydride in the presence of a Lewis-base catalyst.

The starting material dextran has a weight average molecular weight ranging from 40,000 to 80,000 and is commercially available. For example, the dextran having a weight average molecular weight of 70,000 used to prepare the dextran methacrylate monoesters for the working example was obtained from Sigma Chemical Co. (St. Louis, Mo., USA). Dextran is (1–6) linked α-D-glucopyranosyl residues and carries three hydroxyl groups per glucose unit.

The reaction of dextran with methacrylic anhydride is preferably carried out in a dipolar aprotic solvent, e.g., N,N-dimethylformamide (DMF). LiCl is preferably included in the DMF reaction solvent to increase the solubility of dextran in DMF, e.g., at level of 10 weight percent LiCl based on the weight of the DMF. The LiCl does this by forming a salt with DMF and thereby increasing the polarity of the DMF.

The Lewis-base catalyst is preferably triethylamine (TEA).

The reaction can be carried out, for example, at a mole ratio of methacrylic anhydride to hydroxyl groups of dextran ranging from 0.5:1 to 2.0:1, using a mole ratio of triethylamine (TEA) to methacrylic anhydride ranging from 0.01:1 to 0.1:1, reaction temperatures ranging from 40 to 80° C. and reaction times ranging from 5 to 30 hours or more. Various degrees of substitution are obtained by varying reaction temperature, reaction time, reactant ratios and mole ratio of catalyst to methacrylic anhydride. In general, increasing reaction temperature, increasing reaction time, increasing mole ratio of methacrylic anhydride to hydroxyl groups of dextran, and increasing mole ratio of triethylamine to methacrylic anhydride causes an increase in degree of substitution.

For example, for the working example herein, dextran methacrylate monoester of degree of substitution of 0.09 was synthesized by reacting dextran with methacrylic anhydride in a 0.5:1 mole ratio of methacrylic anhydride to hydroxyl groups of dextran, at 60° C. for 10 hours, in the presence of 0.01:1 mole ratio of triethylamine to methacrylic anhydride; dextran methacrylate monoester of degree of substitution of 0.24 was synthesized by reacting dextran with methacrylic anhydride in a 1:1 mole ratio (1 mole of methacrylic anhydride to one hydroxyl group of dextran), at 60° C. for 10 hours in the presence of 1% by weight of triethylamine based on methacrylic anhydride (0.01:1 mole ratio of triethylamine to methacrylic anhydride); and dextran methacrylate monoester of degree of substitution of 0.60 was synthesized by reacting dextran with methacrylic anhydride in a 1:1 mole ratio of methacrylic anhydride to hydroxyl groups of dextran, at 60° C. for 10 hours, in the presence of 0.05:1 mole ratio of triethylamine to methacrylic anhydride.

The degree of substitution obtained is readily calculated from $^1$H-NMR data by integration and normalization of the double bond in the methacrylic acid segment and the hydroxyl hydrogen peaks of the dextran segment and dividing the peak area of the double bond region of the methacrylic acid segment by the peak area of the hydroxyl hydrogen of the dextran segment.

The synthesis of dextran methacrylic acid esters is described in a manuscript cited as Kim, S., et al., "Synthesis and Characterization of Dextran-methacrylate Hydrogel and its Structural Study by SEM" which forms part of U.S. Provisional Application No. 60/160,211, filed Oct. 19, 1999, the whole of which is incorporated herein by reference.

We turn now to the photocrosslinking of the dextran methacrylate monoester (prepared as described above) in solution in a medium containing doxorubicin and drying, the medium being buffered to a pH ranging from 2 to 8.

The medium is preferably an aqueous medium, e.g., phosphate buffer solution (pH 7.4) made by dissolving sodium chloride (120 mmol), potassium chloride (2.7 mmol) and potassium phosphate (10 mmol) in double distilled water (1 liter). A suitable standard buffer solution (pH 3) can be obtained from VWR Scientific Products (West Chester, Pa., USA) under Catalog Number 34170-103.

Preferably the doxorubicin is added to the medium and then dextran methacrylate monoester is dissolved in the medium. The solution is preferably stirred for 2 to 4 minutes to achieve homogeneous distribution of the doxorubicin; the doxorubicin dissolves completely.

The weight ratio of doxorubicin to dextran methacrylate monoester ranges, for example, from 1:200 to 1:2000, in one embodiment from 1:500 to 1:1500. In the working example herein, the weight ratio of doxorubicin to dextran methacrylate monoester used was 1:1000.

Preferably, photoinitiator, e.g., 2,2'-dimethoxy-2-phenylacetophenone (dissolved in N-methyl pyrrolidone) is added in an amount of 0.5% to 5% by weight of the dextran methacrylate monoester.

The photocrosslinking is readily carried out by UV irradiation, e.g., using a long wave UV lamp. Gelation occurs within 5 minutes; however, the irradiation is preferably carried out on a film of the admixture being irradiated, for example, for 1 to 6 hours.

Drying is preferably so that the formed composition is dry to the touch. Drying can be carried out at room temperature, for example, in air and/or in a vacuum oven, e.g., for one day in air at room temperature followed for another day in a vacuum oven at room temperature.

An example of hydrogel without entrapped doxorubicin is schematically shown below.

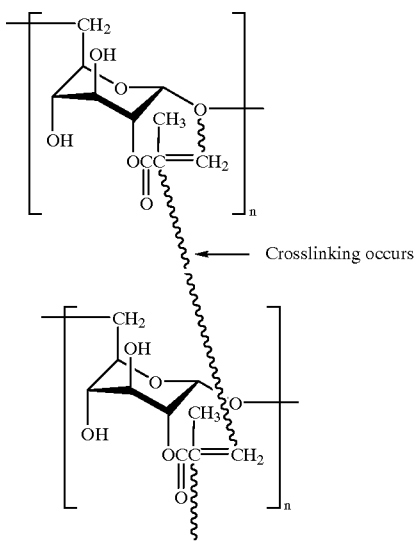

← Crosslinking occurs where n has a range providing the above described molecular weight range, for a degree of substitution of 1.0.

The composition is administered in a dosage of 40 to 90 mg/m$^2$ by oral route of administration or on an implant.

The composition provides a rapid initial release of doxorubicin over a period of 3 to 6 hours followed by slow release. The cumulative release over the initial period is proportional to the square root of time. Increased degree of substitution in the dextran methacrylate monoester decreases cumulative doxorubicin release. The composition provides higher cumulative release in acid pH (e.g., the stomach) than at physiological pH at degrees of substitution less than about 0.4. For dextran methacrylate with a degree of substitution of 0.09 with weight average molecular weight of 70,000 on a dextran basis, the cumulative release rate of doxorubicin at physiological pH was proportional to the square root of time for an initial 5 hour period with a cumulative release of about 92% with very little release thereafter, and at pH of 3 the cumulative release rate of doxorubicin was proportional to the square root of time for an initial 5 hour period with cumulative release of about 87%, increasing to 99% at 240 hours. For dextran methacrylate with a degree of substitution of 0.24 with weight average molecular weight of 70,000 on a dextran basis, the cumulative release rate of doxorubicin at physiological pH was proportional to the square root of time for the first 5 hours, with cumulative release of about 34%, increasing to 47% and reaching equilibrium at 24 hours and at pH 3 the cumulative release rate was proportional to the square root of time for an initial 5 hour period with cumulative release of about 48%, increasing to about 57% at 24 hours and 67% at 240 hours. For dextran methacrylate with degree of substitution of 0.60, with weight average molecular weight of 70,000 on a dextran basis at physiological pH and at pH 3, the cumulative release rate of doxorubicin was proportional to the square root of time for an initial 5 hour period with cumulative release of about 11% at 5 hours, about 27–29% at 24 hours and about 40% at 240 hours with continuing release beyond 240 hours. Thus, lower degrees of substitution provided the least delay and the highest cumulative release so the subset with degree of substitution ranging from 0.05 to 0.15 provides a regimen closest to what is available now.

A description of compositions within the scope of the invention and of testing thereon is included in a manuscript cited as Kim, S., et al., "In Vitro Release Behavior of Dextran-methacrylate hydrogels Using Doxorubicin and Other Model Compounds" which forms part of U.S. Provisional Application No. 60/160,211, filed Oct. 19, 1999, the whole of which is incorporated herein by reference.

The invention is illustrated in the following working example.

EXAMPLE I

Dextran methacrylate monoester with a degree of substitution of 0.09 was synthesized by reacting dextran with methacrylic anhydride in a mole ratio of methacrylic anhydride to hydroxyl groups of dextran of 0.5, at 60° C. for 10 hours, in the presence of 0.01:1 mole ratio of triethylamine to the methacrylic anhydride. Dextran methacrylate monoester with a degree of substitution of 0.24 was synthesized by reacting dextran with methacrylic anhydride in a 1:1 mole ratio of methacrylic anhydride to hydroxyl groups of dextran at 60° C. for 10 hours in the presence of 1% by weight of triethylamine based on methacrylic anhydride. Dextran methacrylate monoester with a degree of substitution of 0.60 was synthesized by reacting dextran with methacrylic anhydride in a mole ratio of methacrylic anhydride to hydroxyl groups of dextran of 1:1, at 60° C. for 10 hours in the presence of 0.05:1 mole ratio of triethylamine to the methacrylic anhydride. In each case, the dextran had a weight average molecular weight of 70,000 and was obtained from Sigma Chemical Company (St. Louis, Mo. USA). In each case, the reaction was carried out in N,N-dimethyl formamide containing 10% by weight LiCl.

In each case, dextran-methacrylate hydrogel with doxorubicin physically entrapped therein was obtained as follows. Dextran methacrylate monoester (1 gram) was dissolved in 2.5 ml pH 7.4 buffer solution (40 w/v %) containing mg of doxorubicin. The buffer solution was phosphate buffer solution made by dissolving sodium chloride (120 mmol), potassium chloride (2.7 mmol), and potassium phosphate (10 mmol) in double distilled water (1 liter). The solution was stirred for a few minutes. Photoinitiator, 2,2'-dimethoxy-2-phenyl acetophenone dissolved in N-methyl pyrrolidone), was then added in amount of 1% by weight of dextran methacrylate monoester and the resulting admixture was stirred rapidly for a few seconds. Resulting solutions were poured onto glass plates, and the films on the plates were irradiated with a 365 nm long wave lamp (8 watts, UVL, 18, UVP, Upland, Calif., USA) for 2 hours. The resulting drug-loaded hydrogel compositions (3 mm thick slab geometry) were dried in air at room temperature for one day and in a vacuum oven at room temperature for another day. The formed compositions had an orange color.

Samples (1 g) consisting of dextran-methacrylate hydrogel (1 gm) with 1 mg doxorubicin entrapped therein were placed in test tubes containing 20 ml of fresh buffer medium (pH 7.4 buffer medium or pH 3 buffer medium). The pH 7.4 buffer medium was the phosphate buffer medium described above and represented physiological pH. The pH 3 buffer medium was obtained from VWR Scientific (West Chester, Pa., USA) under Catalog Number 34170-103. The test tubes were kept at 37° C. in an incubator, and they were gently shaken before an aliquot (1 ml) was removed at each predetermined time. Samples were taken at 1 hour, 2 hours, 3 hours, 4 hours, 5 hours, 24 hours, 48 hours, 72 hours, 144 hours and 240 hours. The visible absorption intensity was measured and the release amount was calculated using an established calibration curve for doxorubicin. For each degree of substitution and pH, there were four measurements from four test tubes for proper statistical average.

Figure 2:
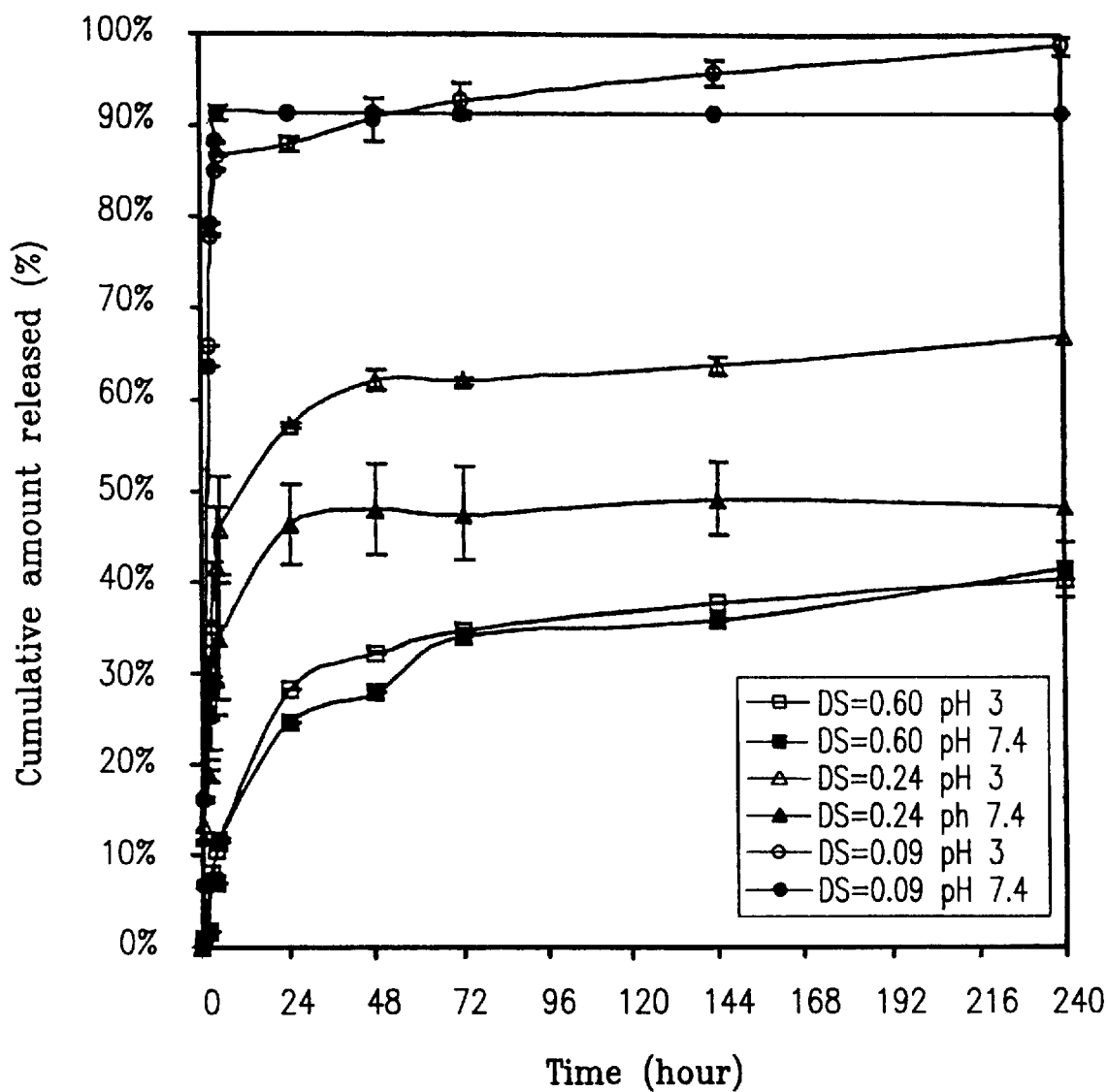
FIG. 2 depicts graphs of cumulative amount of doxorubicin released from dextran-methacrylate hydrogels having different degrees of substitution in different pH media over a 240 hour period, and shows results of Example I.
Figure 3:
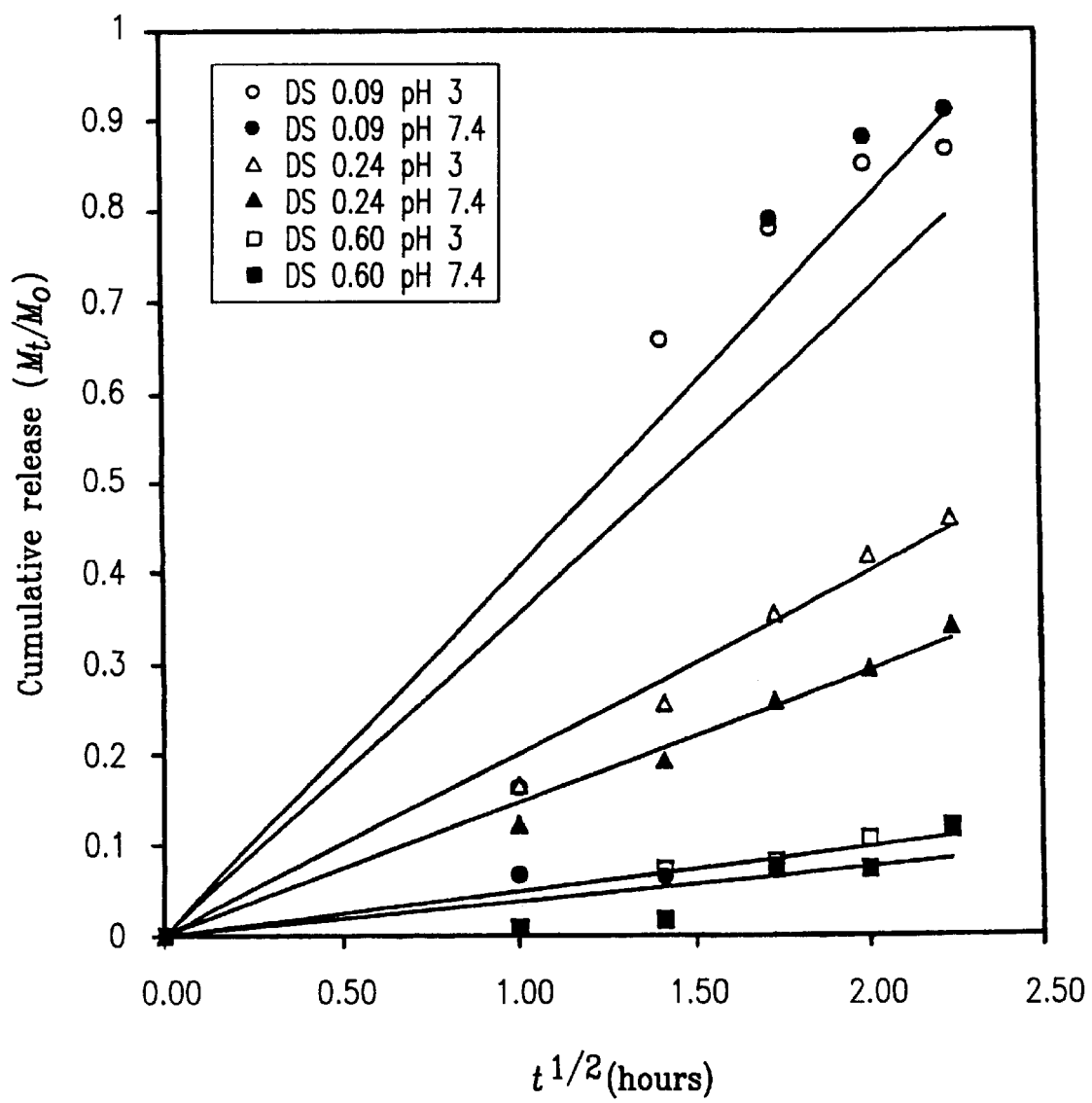
FIG. 3 depicts graphs of cumulative release of doxorubicin ($M_t/M_o$) as a function of square root of time ($t^{1/2}$) from dextran-methacrylate hydrogels with degrees of substitution of 0.09, 0.24, and 0.60 in pH 3.0 and 7.4 media, where $M_t$ is the total amount of drug released in time t and $M_o$ is the total mass of the drug in the sample.

Results are shown in FIGS. 1 through 3.

FIG. 1 is a graph depicting cumulative amount of doxorubicin released from 0.09 degree of substitution hydrogel from 0.24 degree of substitution hydrogel and from 0.60 degree of substitution hydrogel into pH 3 buffer medium and into pH 7.4 buffer medium at 1 hour, 2 hours, 3 hours, 4 hours, 5 hours and 24 hours.

FIG. 2 is a graph depicting cumulative amount of doxorubicin released from 0.09 degree of substitution hydrogel, from 0.24 degree of substitution hydrogel and from 0.60 degree of substitution hydrogel into pH 3 buffer medium and into pH 7.4 buffer medium at 1 hour, 2 hours, 3 hours, 4 hours, 5 hours, 24 hours, 48 hours, 72 hours, 144 hours and 240 hours.

The graphs of FIGS. 1 and 2 show in all cases cumulative release rate of doxorubicin linearly proportioned to the square root of time over an initial 5 hour period.

FIG. 3 depicts graphs of cumulative release of doxorubicin as a function of the time over the initial 5 hours. As shown in FIG. 3, the 0.24 degree of substitution hydrogel showed the closest fit to a linear relationship for both pH 3 and pH 7.4 (in both cases $R^2>0.98$) followed by degree of substitution 0.09 hydrogel ($R^2=0.89$ for pH 3 and $R^2=0.65$ for pH 7.4) and degree of substitution 0.60 hydrogel ($R^2=0.85$ for pH 3 and $R^2=0.69$ for pH 7.4).

As shown in FIGS. 1 and 2, cumulative amount of doxorubicin released from 0.09 degree of substitution hydrogel in physiological pH medium was about 92% at 4 hours and there was very little release thereafter.

As shown in FIGS. 1 and 2, cumulative amount of doxorubicin released from 0.09 degree of substitution hydrogel in pH 3 medium was about 87% at 5 hours, increasing to about 89% at 24 hours and 99% at 240 hours.

As shown in FIGS. 1 and 2, cumulative amount of doxorubicin released from 0.24 degree of substitution hydrogel in physiological pH medium was about 34% at 5 hours, increasing to about 47% and reaching equilibrium at 24 hours.

As shown in FIGS. 1 and 2, cumulative amount of doxorubicin released from 0.24 degree of substitution hydrogel in pH 3 medium was about 47% at 5 hours, increasing to about 57% at 24 hours and 67% at 240 hours.

As shown in FIGS. 1 and 2, cumulative amount of doxorubicin released from 0.60 degree of substitution hydrogel in physiological pH medium was about 11% at 5 hours, increasing to about 27% at 24 hours and about 40% at 240 hours.

As shown in FIGS. 1 and 2, cumulative amount of doxorubicin released from 0.60 degree of substitution hydrogel in pH 3 medium was about 11% at 5 hours, increasing to about 29% at 24 hours and about 40% at 240 hours.

The 0.60 degree of substitution hydrogels continued to release doxorubicin beyond 240 hours.

Diffusion coefficients for the compositions in pH 3.0 and pH 7.4 medium were calculated using Fick's law, that is, $$M_t/M_o = 4(Dt/\pi h^2)^{1/2}$$

where $M_t$ is the amount of drug released in time t, $M_o$ is the total mass of drug in the sample, D is the diffusion coefficient, $\pi$ is 3.14, and h is the thickness of the prepared slab. For degree of substitution 0.09 hydrogel D was 0.293 in pH 3.0 medium and 0.224 in pH 7.4 medium. For degree of substitution 0.24 hydrogel, D was 0.0710 in pH 3.0 medium and 0.0377 in pH 7.4 medium. For degree of substitution 0.60 hydrogel, D was 0.0041 in pH 3.0 medium and 0.0024 in pH 7.4 medium.

VARIATIONS

Many variations of the above will be obvious to those skilled in the art. Thus, the invention is defined by the claims.

What is claimed is:

1. A composition for the controlled release of doxorubicin which comprises doxorubicin physically entrapped in a dextran-methacrylate biodegradable hydrogel.

2. A composition for the controlled release of doxorubicin which comprises doxorubicin physically entrapped in a dextran-methacrylate biodegradable hydrogel which is obtainable by photocrosslinking dextran methacrylate monoester in solution in a medium containing doxorubicin and drying the composition formed by the photocrosslinking of dextran-methacrylate monoester in solution in a medium containing doxorubicin until said composition is dry to the touch, the dextran methacrylate monoester having an average degree of substitution of each α-D-glucopyranosyl of dextran by methacrylic acid ranging from 0.05 to 0.75 and a weight average molecular weight ranging from 40,000 to 80,000 on a dextran basis, said medium being buffered to a pH ranging from 2 to 8, the weight ratio of doxorubicin to dextran methacrylate monoester ranging from 1:200 to 1:2000.

3. The composition for the controlled release of doxorubicin as claimed in claim 2, wherein the weight ratio of doxorubicin to dextran methacrylate monoester ranges from 1:500 to 1:1500.

4. The composition for the controlled release of doxorubicin as claimed in claim 3, wherein the dextran methacrylate monoester which is photocrosslinked has an average degree of substitution ranging from 0.05 to 0.15.

5. The composition for the controlled release of doxorubicin as claimed in claim 4, wherein the dextran methacrylate monoester which is photocrosslinked has a weight average molecular weight of 70,000 on a dextran basis.

6. The composition for the controlled release of doxorubicin as claimed in claim 3, wherein the dextran methacrylate monoester which is photocrosslinked has an average degree of substitution ranging from 0.15 to 0.40.

7. The composition for the controlled release of doxorubicin as claimed in claim 6, wherein the dextran methacrylate monoester which is photocrosslinked has a weight average molecular weight of 70,000 on a dextran basis.

8. The composition for the controlled release of doxorubicin as claimed in claim 3, wherein the dextran methacrylate monoester which is photocrosslinked has an average degree of substitution ranging from 0.40 to 0.75.

9. The composition for the controlled release of doxorubicin as claimed in claim 8, wherein the dextran methacrylate monoester which is photocrosslinked has a weight average molecular weight of 70,000 on a dextran basis.

10. The composition for the controlled release of doxorubicin as claimed in claim 3, wherein the dextran methacrylate monoester which is photocrosslinked has a weight average molecular weight of 70,000 on a dextran basis.

11. The composition for the controlled release of doxorubicin as claimed in claim 2 where the weight average molecular weight ranges from 50,000 to 80,000 on a dextran basis.

12. The composition for the controlled release of doxorubicin as claimed in claim 2 where the dextran-methacrylate monoester is obtainable by reaction of dextran with methacrylic anhydride in the presence of a Lewis-base catalyst.

* * * * *